United States Patent
Yanagida

(10) Patent No.: US 9,272,245 B2
(45) Date of Patent: Mar. 1, 2016

(54) FILTRATION METHOD

(75) Inventor: Koichiro Yanagida, Tokyo (JP)

(73) Assignee: ASAHI KASEI MEDICAL CO., LTD., Tokyo (JP)

(*) Notice: Subject to any disclaimer, the term of this patent is extended or adjusted under 35 U.S.C. 154(b) by 936 days.

(21) Appl. No.: 12/993,512

(22) PCT Filed: Apr. 30, 2009

(86) PCT No.: PCT/JP2009/001944
§ 371 (c)(1),
(2), (4) Date: Feb. 14, 2011

(87) PCT Pub. No.: WO2009/141965
PCT Pub. Date: Nov. 26, 2009

(65) Prior Publication Data
US 2011/0166326 A1    Jul. 7, 2011

(30) Foreign Application Priority Data

May 22, 2008  (JP) ................................ 2008-133925

(51) Int. Cl.
| B01D 69/08 | (2006.01) |
| B01D 69/12 | (2006.01) |
| B01D 71/34 | (2006.01) |
| B01D 71/68 | (2006.01) |
| B01D 71/82 | (2006.01) |
| C07K 1/00 | (2006.01) |
| B01D 61/14 | (2006.01) |
| A61L 2/00 | (2006.01) |
| B01D 61/22 | (2006.01) |
| B01D 67/00 | (2006.01) |
| B01D 69/02 | (2006.01) |
| C07K 1/34 | (2006.01) |

(52) U.S. Cl.
CPC ............. *B01D 61/145* (2013.01); *A61L 2/0017* (2013.01); *B01D 61/22* (2013.01); *B01D 67/0093* (2013.01); *B01D 69/02* (2013.01); *B01D 69/08* (2013.01); *B01D 69/12* (2013.01); *B01D 71/34* (2013.01); *B01D 71/68* (2013.01); *C07K 1/34* (2013.01); *B01D 2323/02* (2013.01); *B01D 2323/38* (2013.01); *B01D 2325/04* (2013.01); *B01D 2325/20* (2013.01); *B01D 2325/36* (2013.01)

(58) Field of Classification Search
None
See application file for complete search history.

(56) References Cited

U.S. PATENT DOCUMENTS

| 5,017,292 A | 5/1991 | DiLeo et al. |
| 2002/0193752 A1* | 12/2002 | Lynn .......................... 604/249 |
| 2004/0023017 A1 | 2/2004 | Nagoya |
| 2007/0043216 A1* | 2/2007 | Bair et al. .................... 536/25.4 |
| 2010/0096328 A1* | 4/2010 | Hamasaki et al. ............ 210/638 |
| 2010/0190965 A1 | 7/2010 | Yamaguchi et al. |

FOREIGN PATENT DOCUMENTS

| CN | 1705505 | 12/2005 |
| EP | 1 552 878 | 7/2005 |
| JP | 07-071624 | 8/1995 |
| JP | 11-508813 | 8/1999 |
| JP | 2000-5569 | 1/2000 |
| JP | 2004-89155 | 3/2004 |
| JP | 2004-277323 | 10/2004 |
| WO | 91/16968 | 11/1991 |
| WO | 96/39208 | 12/1996 |
| WO | 2004/035180 | 4/2004 |
| WO | 2008/156124 | 12/2008 |

OTHER PUBLICATIONS

Hongo-Hirasaki et al. "Removal of small viruses (parvovirus) from IgG solution by virus removal filter PlanovaR20N" J. Membrane Science, 278 2006, pp. 3-9.*
International Search Report for PCT/JP2009/001944, mailed Aug. 11, 2009.
International Preliminary Report on Patentability for PCT/JP2009/001944, mailed Jan. 20, 2011.
Extended European Search Report that issued with respect to corresponding European Patent Application No. 09750327.0, dated Jun. 6, 2012.
Japan Office action, mail date is Aug. 6, 2013.

* cited by examiner

*Primary Examiner* — Daniel E Kolker
*Assistant Examiner* — James Rogers
(74) *Attorney, Agent, or Firm* — Greenblum & Bernstein, P.L.C.

(57) ABSTRACT

Provided is a filtration method for the step of removing viruses in a process of producing a protein preparation during which an intermediate protein preparation with a high protein concentration flows at high pressure to a virus removal filter. The filtration method employs a virus removal filter which has a close fitting nozzle of which the inlet at least has a pressure resistance of 600 kPa or more, and an effective area of the virus removal membrane of at least 0.0001 m$^2$ and no more than 0.03 m$^2$. An intermediate protein preparation with the protein concentration raised to at least 20 mg/ml and no more than 100 mg/ml by means of a purification process flows down to said virus removal filter under conditions in which the inlet pressure of the intermediate protein preparation is at least 150 kPa and no more than 600 kPa, the average protein filtration speed is at least 1.0 kg/m$^2$/hr, and the filtration time is at least 1 hour and no more than 5 hours, to give an intermediate protein preparation filtrate with a viral removal rate (LRV) of ≥3.

6 Claims, No Drawings

FILTRATION METHOD

TECHNICAL FIELD

The present invention relates to a filtration method for filtering an intermediate product of a protein product in a virus removal step in a product process of the protein product, and a virus removal filter used therefor.

BACKGROUND ART

A protein product, such as antibody drug, recombinant protein drug, plasma product, plasma fractionation product or the like may be contaminated with viruses derived from a raw material or caused during a production process. Therefore, it is necessary to inactivate or remove viruses in the course of preparing the protein product.

As the method for inactivating viruses that may be mixed into a protein product a heat treatment, a chemical treatment, or the like have been conducted. However, viruses may not be sufficiently inactivated using only such a treatment alone. Moreover, useful proteins themselves contained in a protein product may be denatured during such a treatment. In view of this situation, as a physical virus removal means that do not cause chemical denaturation separation/removal of viruses using a filter membrane have been carried out.

A membrane formed of a natural material such as cellulose and a virus removal membrane formed of a synthetic polymer material such as polyvinylidene fluoride (PVDF) or polyethersulfone (PES) have been known as a virus removal filter membrane (see Non-patent Documents 1 to 4).

When filtering an intermediate product of a protein product (hereinafter, may be referred to as an "intermediate protein product") using a virus removal apparatus that is provided with these virus removal membranes, it is ideal that a large amount of proteins can be filtered within a short time, and viruses can be removed by a sufficiently high virus removal performance. However in fact though a cellulose membrane, for example, can filter the intermediate protein product without clogging even at a protein concentration of 20 mg/ml or more, allows the practical pressure to be increased to only about 100 kPa due to low pressure resistance. On the other hand, a synthetic polymer membrane allows the practical pressure to be increased to about 300 kPa without problems due to high pressure resistance thereof, but may clog when the protein concentration is increased to about 20 mg/ml and cannot filter. Therefore, the intermediate protein product has been commonly filtered at a low protein concentration of 10 mg/ml or less (see Patent Document 1).

For these reasons, research of a filtration method carrying out under filtration conditions where an intermediate protein product having a high protein concentration that is increased by purification steps, such as various chromatographies, ultrafiltration and the like is passed through a virus removal apparatus at a high pressure have not been developed, and a virus removal filter used suitably for such a method also have not been developed.

Since an intermediate protein product is an important material for preparing a protein product, it is temporally and economically difficult to determine the filtration method and the operating conditions for the virus removal step in a production scale. Therefore, the inventor strongly recognized that it is very important to previously determine the filtration method for the virus removal step, the protein concentration of the intermediate protein product, and the operating conditions of the inlet pressure of the virus removal filter, and/or the filtration time in a small scale, and apply them to the scale-uped protein product production process.

[Patent Document 1] JP-A-2004-277323
[Non-patent Document 1] Manabe S., Removal of virus through novel membrane filtration method, Dev. Biol. Stand., (1996) 88: 81-90
[Non-patent Document 2] Brandwein H. et al., Membrane filtration for virus removal, Dev Biol (Basel), (2000) 102: 157-63
[Non-patent Document 3] Aranha-Creado et al., Clearance of murine leukaemia virus from monoclonal antibody solution by a hydrophilic PVDF microporous membrane filter, Biologicals, June 1998, 26 (2): 167-72
[Non-patent Document 4] L. Moce-Llivina et al., Comparison of polyvinylidene fluoride and polyether sulfone membranes in filtering viral suspensions, Journal of Virological Methods, April 2003, Vol. 109, Issue 1, pages 99-101

DISCLOSURE OF THE INVENTION

Problems to be Solved by the Invention

In view of the above situation, an object of the present invention is to provide a filtration method for filtering an intermediate protein product having a high protein concentration under the condition that the intermediate protein product is passed through a virus removal filter at a high pressure during a virus removal step in a protein product producing process, and provide a virus removal filter used therefor.

Means for Solving the Problems

The inventor conducted extensive studies in order to achieve the above object. As a result, the inventor found that the protein concentration of an intermediate protein product, and the operating conditions of the inlet pressure of a virus removal filter and/or the filtration time, when a virus removal process for an intermediate protein product is scaled up to an industrial scale, can be determined by using a filtration method that includes passing the intermediate protein product for 1 to 5 hours through the virus removal filter, the intermediate protein product having a protein concentration of 20 to 100 mg/ml that has been increased by purification process previously under the condition of an inlet pressure of the intermediate protein product of 150 to 600 kPa and an average protein filtration rate of 1.0 kg/m$^2$/Hr or more to obtain a filtrate of the intermediate protein product having a virus removal rate (LRV) of 3 or more, wherein the virus removal filter comprises a container that has at least one inlet and at least one outlet, and a virus removal membrane for removing viruses from the intermediate protein product, the space inside the container is divided by the virus removal membrane into an inlet-side space and an outlet-side space, at least the inlet has a nozzle having a fitting structure that has a pressure resistance of 600 kPa or more, and the virus removal membrane has an effective membrane area of 0.0001 to 0.03 m$^2$. The inventor found that the above method is also useful for the facility design for the virus removal step. These findings have led to the completion of the present invention.

Specifically, the present invention includes the following.

[1] A filtration method for filtering an intermediate protein product having a predetermined protein concentration through a virus removal filter at a predetermined pressure, comprising (1) using the virus removal filter that comprises a container that has at least one inlet and at least one outlet, and a virus removal membrane for removing viruses from the intermediate protein product, the space inside the container is divided by the virus removal membrane into an inlet-side space and an outlet-side space, at least the inlet of the container has a nozzle having a fitting structure that has a pressure resistance of 600 kPa or more, and the virus removal membrane has an effective membrane area of 0.0001 to 0.03 $m^2$, (2) passing the intermediate protein product for 1 to 5 hours through the virus removal filter, the intermediate protein product having a protein concentration of 20 to 100 mg/ml that has been increased by purification process previous to (2) passing, at an inlet pressure of the intermediate protein product of 150 to 600 kPa and an average protein filtration rate of 1.0 kg/$m^2$/Hr or more, (3) obtaining a filtrate of the intermediate protein product having a virus removal rate (LRV: logarithmic reduction value) of 3 or more.

[2] The filtration method according to [1], comprising
(4) passing the intermediate protein product for 3 to 5 hours through the virus removal filter, the intermediate protein product having a protein concentration of 20 to 100 mg/ml that has been increased by purification process previous to (4) passing, at an inlet pressure of the intermediate protein product of 150 to 600 kPa and an average protein filtration rate of 1.0 kg/$m^2$/Hr or more, and
(5) obtaining a filtrate of the intermediate protein product having the virus removal rate (LRV) of 3 or more.

[3] The filtration method according to [1] or [2], wherein the virus is selected from Parvoviridae, Retroviridae, Flaviviridae, Reoviridae, Paramyxoviridae, Herpesviridae, Picornaviridae, and Papovaviridae.

[4] The filtration method according to any one of [1] to [3], wherein the protein in the intermediate protein product is an immunoglobulin.

[5] The filtration method according to [4], wherein the immunoglobulin is immunoglobulin G.

[6] The filtration method according to any one of [1] to [5], wherein the virus removal membrane is made of a hydrophilized synthetic polymer.

[7] The filtration method according to any one of [1] to [6], wherein the virus removal membrane is a hollow fiber virus removal membrane.

[8] A method comprising applying the protein concentration and the inlet pressure in the filtration method according to any one of [1] to [7] as a scale-uped operating condition.

[9] The method according to [8], further comprising applying the filtration time of the filtration method according to any one of [1] to [7] as a scale-uped operating condition.

[10] A virus removal filter used for the filtration method according to any one of [1] to [7], comprising a container that has at least one inlet and at least one outlet, and a virus removal membrane for removing viruses from the intermediate protein product, wherein the space inside the container is divided by the virus removal membrane into an inlet-side space and an outlet-side space, at least the inlet of the container has a nozzle having a fitting structure that has a pressure resistance of 600 kPa or more, and the virus removal membrane has an effective membrane area of 0.0001 to 0.03 $m^2$.

[11] The virus removal filter according to [10], wherein the virus removal membrane is a hollow fiber virus removal membrane.

[12] The virus removal filter according to [10] or [11], wherein the virus removal membrane is a multilayer microporous membrane that includes a thermoplastic resin and has a coarse structure layer having a high porosity and a fine structure layer having a low porosity, the coarse structure layer being present on at least one surface of the membrane, and having a thickness of 5.0 μm or more, the fine structure layer having a thickness of 50% or more of the thickness of the entire membrane, and the coarse structure layer and the fine structure layer being integrated.

Effects of the Invention

The operating conditions for the virus removal step in a protein product producing process under conditions where an intermediate protein product having a high protein concentration is passed through a virus removal filter at a high pressure can be determined using the filtration method according to the present invention. Specifically, the filtration method employed in the virus removal step, the protein concentration of the intermediate protein product, and the operating condition of the inlet pressure of the virus removal filter, and/or the filtration time are determined in advance, and may be applied to a scale-uped protein product production process. In this case, it suffices to increase the membrane area of the virus removal filter in proportion to the increasing rate in the volume of the intermediate protein product.

As an associated effect, the filtration method according to the present invention may also be used to improve the virus removal step in the protein product producing process so that a virus removal step that allows production of a larger amount of protein products within a shorter time can be designed.

BEST MODE FOR CARRYING OUT THE INVENTION

When determining the operating conditions for the virus removal step in the protein product producing process, the average protein filtration rate of the intermediate protein product and the virus removal rate are important factors. The filtration rate normally has a negative correlation with the protein concentration. Therefore, the filtration rate decreases as the protein concentration increases so that the filtration time unpreferably increases. If a dilution step is added in order to decrease the protein concentration, the installation cost unpreferably increases. In order to filter the intermediate protein product while remaining its high protein concentration without causing a decrease in filtration rate, the intermediate protein product may be filtered using a virus removal filter that comprises a container that has at least one inlet and at least one outlet for the intermediate protein product, and a virus removal membrane for removing viruses, wherein the space inside the container is divided by the virus removal membrane into an inlet-side space and an outlet-side space for the intermediate protein product, and the inlet of the container is a nozzle having a fitting structure that has a pressure resistance of 600 kPa or more, provided that the entire virus removal filter has a pressure resistance of 600 kPa or more.

Examples of the nozzle having a fitting structure that has a pressure resistance of 600 kPa or more include, for example, a luer lock nozzle, a one-touch nozzle (e.g., Inch-size One-touch Mini, Inch-size One-touch Fitting, and One-touch Mini (all registered trademark) manufactured by SMC, for example), a coupler nozzle, a ferrule nozzle, and the like and these are usable. Note that except for the above nozzles, any nozzle that has a fitting structure having a pressure resistance of 600 kPa or more and can supply a filtrate without leakage may be used in the present invention.

The virus removal membrane must have an effective membrane area of 0.0001 to 0.03 $m^2$. If the effective membrane area of the virus removal membrane is larger than 0.03 $m^2$, a large amount of intermediate protein product may be required for filtration, so that the evaluation cost may increase. If the effective membrane area of the virus removal membrane is less than 0.0001 m², the volume of the intermediate protein product used to evaluate the virus removal performance may decrease too much due to a decrease in filtration amount, so that it may be difficult to quantitatively determine viruses. Therefore, the effective membrane area of the virus removal membrane is suitably 0.0001 to 0.03 m². The effective membrane area of the virus removal membrane is preferably 0.0003 to 0.02 m², more preferably 0.0005 to 0.01 m², and most preferably 0.0007 to 0.002 m².

Note that the effective membrane area of the virus removal membrane refers to the surface area of the virus removal membrane where the intermediate protein product can pass through. When the virus removal membrane is a hollow fiber membrane and the intermediate protein product passes through the membrane from the inner side to the outer side, the effective membrane area of the virus removal membrane refers to the area of the portion where the intermediate protein product can pass through in the inner surface area of the virus removal membrane. When the intermediate protein product passes through the membrane from the outer side to the inner side, the effective membrane area of the virus removal membrane refers to the area of the portion where the intermediate protein product can pass through in the outer surface area of the virus removal membrane. When the virus removal membrane is a flat membrane, the effective membrane area of the virus removal membrane refers to the area of the portion where the intermediate protein product can pass through in the surface area of the virus removal membrane.

When using a hollow fiber membrane filter, the effective membrane area of the virus removal membrane may be easily controlled by increasing or decreasing the number of hollow fibers, it can be thus easily scaled up or down. In addition, it is easy to obtain scalability since no major disturbance factor occurs when scaling up or down. Specifically, in the case of the hollow fiber membrane filter, if the membrane area of the hollow fiber membrane filter changes, only the filtration volume changes and the filtration performance may be thought to maintain. The increases or decreases of the membrane area affect the increase or decrease in the filtrate amount. If the amount of filtrate is too small, negative effects may be occur in quantitative determination of viruses. If the amount of filtrate is too large, convenience of the operation and cost may be adversely affected as described above. In the case where a flat membrane is used, significant scale-up may be need to change the shape of the membrane (e.g., from a disk shape to a tubular shape). However, the effect thereof is similarly limited. The process design of the virus removal step in a protein product production process can be implemented in a small scale not in an actual production scale depending upon the reliability of scalability.

A filter having the above structure may be used as the virus removal filter. The membrane having a flat membrane structure or a hollow fiber membrane structure may be used, of these the hollow fiber membrane structure is preferable. A material having a pressure resistance of 600 kPa or more may be used as the material for the membrane. For example, it is preferable to use a membrane that is formed of a synthetic polymer, such as polyvinylidene fluoride (PVDF), polyethersulfone (PES), or polysulfone (PS) and has hydrophilicity. Note that it is important that the membrane have a pressure resistance of 600 kPa or more.

Many methods are known as methods for hydrophilizing a membrane formed of a synthetic polymer, such as a method of graft-polymerizing a hydrophilic vinyl monomer with one vinyl group onto the pore surface of a microporous membrane at a graft ratio of 3 to 50% (WO2004/035180), a method of bonding a polymer formed of a polyfunctional acrylate or methacrylate to a membrane via a crosslinking agent (JP-A-2000-1548), or a method of impregnating a membrane with a solution including a polymerization initiator and a hydrophilic monomer, and polymerizing the monomer inside the pores of the membrane (WO91/16968), or the like. The purpose to make have hydrophilicity is to improve filterability of the membrane formed of a hydrophobic synthetic polymer with respect to the intermediate protein product. Therefore, the hydrophilization method is not limited to those described herein.

Note that the graft ratio used herein is defined by the following expression.

$$\text{Graft ratio (\%)} = 100 \times [(\text{mass of membrane after grafting} - \text{mass of membrane before grafting})/(\text{mass of membrane before grafting})]$$

It is preferable that the membrane have a gradient structure in which a coarse structure layer that has a large pore size and a high porosity is present on the upstream side and a fine structure layer that has a small pore size and a low porosity is thus suitable for virus removal is present on the downstream side according to the protein preparation intermediate product flow direction, wherein the pore size continuously changes in the connection between the coarse structure layer and the fine structure layer.

It is more preferable that the membrane be a microporous membrane which comprises a thermoplastic resin and has a coarse structure layer having a high porosity and a fine structure layer having a low porosity, and that the microporous membrane is a multilayer microporous membrane which has the coarse structure layer having a thickness of 5.0 μm or more on at least one surface of the membrane, and has the fine structure layer having a thickness of 50% or more of the thickness of the entire membrane, and the coarse structure layer and the fine structure layer is integrated.

In addition the coarse structure layer preferably has a gradient structure in which the local porosity continuously decreases from the surface of the membrane toward the fine structure layer, and is preferably present on only one surface of the membrane. Such a membrane may be produced by the method disclosed in JP-A-H11-319522, JP-A-H09-169867, or WO2004/035180, for example.

Viruses used for evaluation may be arbitrarily selected from relevant viruses that may be contaminated into a protein product, specific model viruses, and non-specific model viruses. The terms "relevant virus", "specific model virus", and "non-specific model virus" used herein refer to those defined in the guideline of the International Conference on Harmonization of Technical Requirements for Registration of Pharmaceuticals for Human Use (ICH). Specifically, the term "relevant virus" refers to a virus or a virus of the same species that is known or likely to present as mixture in a cell substrate or any other reagents or materials used in a protein product production process. The term "specific model virus" refers to a virus that is closely related to a known or suspected virus. Specifically, it is defined as a virus of same genus or family, and the virus has physical and chemical properties similar to those of the observed or suspected virus. The term "non-specific model virus" refers to a virus that is used for characterization test of viral clearance of a production process in order to characterize how much ability about removal or inactivation of the viruses the production process generally has (i.e., characterize the robustness of the process in an aspect that the process surely exerts viral clearance performance).

For example, when producing a product using a mouse-derived substrate, such as monoclonal antibody or the like, a retrovirus, such as murine leukemia virus or the like, a parvovirus, such as minute virus of mice or the like, or a flavivirus, such as bovine diarrhea virus or the like may be used as the relevant virus or the specific model virus. As the non-specific model virus, a parvovirus, such as porcine parvovirus or the like may also be used as the smallest virus model.

When producing a product using a human plasma-derived substrate, such as plasma fractionation product or the like, a human parvovirus B19 (Parvoviridae), an HIV virus (Retroviridae), a porcine parvovirus (Parvoviridae), and a bovine diarrhea virus (Flaviviridae) may be used as the relevant virus, specific model virus of a human parvovirus B19, and specific model virus of hepatitis C virus, respectively. Similarly, the virus may also be used by selecting from Herpesviridae, such as herpes simplex virus, pseudorabies virus or the like, Paramyxoviridae, such as parainfluenza virus or the like, Reoviridae, such as reovirus type 3 or the like, Picornaviridae, such as poliovirus or the like, Papovaviridae, such as SV-40 virus or the like, and the like. The selection of the virus used should be determined based on known requirements described in the ICH or the like.

These viruses used for evaluation are added to the intermediate protein product in a predetermined certain amount, and the amounts of viruses are measured before and after filtration using the virus removal filter to determine the virus removal performance. The amount of viruses added to the intermediate protein product may be calculated back from the required virus removal rate. Note that the filter may clog due to impurities contained in the virus solution so that the filtration test may be adversely affected. Therefore, it is desirable to adjust the amount of viruses added to the intermediate protein product based on the purity of the virus solution. When the virus solution has been purified, the virus solution may be added in an amount of 10 vol % or less, preferably 5 vol % or less, and more preferably 1 vol % or less, with respect the volume of the intermediate protein product. When the virus solution has not been purified and contains a large amount of impurities, the virus solution is preferably added in an small amount of 1 vol % or less, preferably 0.5 vol % or less, and more preferably 0.1 vol % or less. Note that it is desirable to add the virus solution in an amount equal to or more than the detectable minimal amount of a virus removal rate (LRV) of 3 or more.

The term "virus removal rate (LRV)" used herein refers to a logarithmic value of the decreasing ratio of the amount of viruses contained in the solution after filtration with the virus removal filter with respect to the amount of viruses contained in the solution before filtration. For example, the virus removal rate (LRV: logarithmic reduction value) may be calculated by the following expression.

$$LRV = \log_{10} A - \log_{10} B$$

where, A is the virus concentration in the solution before filtration, and B is the virus concentration in the solution after filtration with the virus removal filter.

The solution may contain a large amount of impurities depending on the preparation method of virus, so that the filtration rate may be adversely affected to a large extent. In such case, the solution may be used after separating impurities by purification. As a purification method of viruses a method using ultracentrifugation or the like has been already well known.

The operating conditions are set so that the virus removal rate of the virus removal filter satisfies LRV of 3 or more. The virus removal rate (LRV) of viruses larger than the pore size of the virus removal filter is normally 3 or more, and the virus removal rate (LRV) of viruses smaller than the pore size of the virus removal filter is normally less than 3 (Hironari Izumi et al., Viral Safety of Plasma-Derived Blood Products. II. Effect of Virus Elimination by Nanofiltration on Monoclonal-Purified Freeze-Dried Coagulation Factor VIII Concentrate (CROSS EIGHT M (registered trademark)) and Intramuscular Human Immunoglobulin (Anti-HBs Human Immune Globulin "Nisseki" (registered trademark) and Human Immune Globulin "Nisseki" (registered trademark), Japanese Journal of Transfusion Medicine, (1999), Vol. 45. No. 3, pages 357-361). The virus removal rate (LRV) does not necessarily become zero, and a certain level (3 or less) of a virus removal rate (LRV) may be obtained. This is considered to be based on partial aggregation or adsorption of the virus molecules, not the virus removal rate due to size separation that the virus removal filter inherently possesses. Therefore, when it is desired to remove viruses having a size equal to or larger than the pore size of the virus removal filter, the virus removal rate (LRV) must satisfy 3 or more.

The intermediate protein product used for the filtration method according to the present invention may include an intermediate antibody product, an intermediate recombinant protein product, an intermediate plasma product, an intermediate plasma fractionation product, or the like. The intermediate immunoglobulin product is particularly preferable. The more preferable intermediate protein product is an intermediate immunoglobulin G product, and most preferable is an intermediate immunoglobulin G monoclonal antibody product.

The intermediate protein product is filtered through the virus removal filter without adding viruses at first, and the average protein filtration rate of the intermediate protein product is evaluated. The average protein filtration rate (kg/m$^2$/Hr) is evaluated by filtering the intermediate protein product having a protein concentration of 20 to 100 mg/ml under the high pressure condition of an inlet pressure of the intermediate protein product of 150 to 600 kPa for 1 to 5 hours. After ensuring the protein concentration and the pressure at which an average protein filtration rate of 1.0 kg/m$^2$/Hr or more is achieved, a predetermined amount of viruses are added to the intermediate protein product, and the intermediate protein product is filtered through the virus removal filter within the range of the protein concentration and the pressure to evaluate the virus removal performance of the virus removal step.

The amount of protein products produced by a single batch operation tends to increase in total weight. As to the total amount (total weight) of protein products produced by a single batch operation, for example, high production ability of 50 kg or more per one batch has been achieved in antibody drug product field due to an improvement in productivity. It is desirable to complete the virus removal step within one day even in the protein product having such high production ability from the viewpoint of the stability of the intermediate protein product and the efficiency of the production process. The average protein filtration rate of the virus removal filter must be 1.0 kg/m$^2$/Hr or more therefore. If the average protein filtration rate of the virus removal filter is 1.0 kg/m$^2$/Hr or more, 50 kg of the intermediate protein product can be filtered within 12.5 hours using one 4 m$^2$ filter, and filtered within 6.25 hours using two 4 m$^2$ filters.

After determining the protein concentration and the pressure at which an average protein filtration rate of 1.0 kg/m$^2$/Hr or more is achieved, a predetermined amount of viruses are added to the intermediate protein product, and the intermediate protein product is filtered through the virus removal filter within the range of the protein concentration and the pressure to evaluate the virus removal performance of the virus removal step. Specifically, a protein concentration and an inlet pressure of the intermediate protein product at which a virus removal rate (LRV) of 3 or more is achieved are selected. When filtering the intermediate protein product having a high protein concentration of 20 to 100 mg/ml under a high pressure of 150 to 600 kPa at an inlet of the intermediate protein product, the operating conditions, where an average protein filtration rate of 1.0 kg/m$^2$/Hr or more and a virus removal rate (LRV) of 3 or more are achieved, are ensured, and installation conditions, operating conditions, and the like after scale-up are estimated. Note that the average protein filtration rate may not be measured in a state in which the virus solution is not added, the average protein filtration rate also may be measured simultaneously in a system which the virus solution is added.

An increase in cost due to the scale-up of the filtration apparatus, container, pipe, and the like can be advantageously prevented by filtering an intermediate protein product at a higher protein concentration. On the other hand, stability problems may occur when the protein concentration is too high. Therefore, the protein concentration is 20 to 100 mg/ml, preferably 25 to 100 mg/ml, more preferably 30 to 100 mg/ml, and most preferably 30 to 50 mg/ml.

The intermediate protein product can be filtered rapidly within a short time by increasing the inlet pressure. However, the apparatus may be damaged, or risky leakage may occur if the inlet pressure is increased too high. Therefore, the filtration is carried out at the inlet pressure of 150 to 600 kPa. The inlet pressure is preferably 196 to 500 kPa, more preferably 245 to 400 kPa, still more preferably 294 to 400 kPa, and most preferably 294 to 300 kPa. The protein concentration and the inlet pressure are preferably evaluated while altering these operating parameters within the above range so that an average protein filtration rate of 1.0 kg/m$^2$/Hr or more and a virus removal rate (LRV) of 3 or more are satisfied simultaneously.

The filtration time that the intermediate protein product is passed through the virus removal filter is 1 to 5 hours. Note that the filtration time may be set to a short time when it is desired to complete a scale-uped virus removal step in the protein product production process within a short time even if the membrane area of the virus removal filter is increased, and may be set to a long time when it is desired to decrease the effective membrane area of the virus removal membrane. In order to determine conditions where a virus removal rate (LRV) of 3 or more is satisfied even after 3 hours from the beginning of the filtration, the intermediate protein product may be preferably passed through the virus removal filter for 3 to 5 hours.

EXAMPLES

The present invention is described in further detail below by way of examples.

Example 1

A virus removal filter produced by the method disclosed in Example 1 of WO2004/035180 was used. Specifically, the virus removal filter was formed of a hydrophilized microporous hollow fiber membrane (effective membrane area: 0.001 m$^2$), and had a luer lock nozzle having a pressure resistance of 600 kPa or more at the inlet, wherein the space inside the container (virus removal filter housing) was divided by the hollow fiber membrane into an inlet-side space and an outlet-side space. The hydrophilized microporous hollow fiber membrane was obtained by graft-polymerizing, so as to obtain the graft ratio of 10%, a hydrophilic vinyl monomer (hydroxypropyl acrylate) onto a microporous hollow fiber membrane formed of polyvinylidene fluoride and having a pressure resistance of 600 kPa or more. The hollow fiber membrane was a multilayer microporous membrane having a coarse structure layer having a high porosity, being present on the inner surface of the hollow fiber membrane, and having a thickness of 7.0 μm, and a dense structure layer having a low porosity having a thickness of 80% of the thickness of the entire membrane, and the coarse structure layer and the fine structure layer being integrated. A human immunoglobulin G solution having a human immunoglobulin G concentration of 30 mg/ml (solvent: 0.1 M saline solution) was used as a model of an intermediate protein product. After the addition of 0.5 vol % of a porcine parvovirus (PPV) solution to the human immunoglobulin G solution, the mixture was pre-filtered through a hollow fiber membrane filter having a pore size of 35 nm ("PLANOVA (registered trademark) 35N" manufactured by Asahi Kasei Medical Co., Ltd.). The immunoglobulin concentration and the PPV concentration after the pre-filtration were 30 mg/ml and 6.1 (TCID$_{50}$/ml), respectively.

The PPV-containing human immunoglobulin G solution (30 mg/ml) was subjected to dead-end filtration for 5 hours at a pressure of 294 kPa using the above virus removal filter. The average protein filtration rates measured after 3, 4 and 5 hours of filtration were 1.9, 1.9 and 1.8 kg/m$^2$/Hr, respectively. Specifically, the virus removal rate could be evaluated using a filtrate obtained at a high rate filtration rate of 1.0 kg/m$^2$/Hr or more in all above measuring points. The all virus removal rates (LRV) measured using the filtrates obtained after 1, 3 and 5 hour of filtration were 5.6 or more.

A protein concentration of the intermediate protein product of 30 mg/ml, an inlet pressure of the virus removal filter of 294 kPa, and a filtration time of 5 hours or less could be determined as the operating conditions for the virus removal step.

Examples 2 to 4

A virus removal filter produced by the method disclosed in Example 1 of WO2004/035180 was used. Specifically, the virus removal filter was formed of a hydrophilized microporous hollow fiber membrane (effective membrane area: 0.001 m$^2$), and had a luer lock nozzle having a pressure resistance of 600 kPa or more at the inlet, wherein the space inside the container was divided by the hollow fiber membrane into an inlet-side space and an outlet-side space. The hydrophilized microporous hollow fiber membrane was obtained by graft-polymerizing (graft ratio: 10%) a hydrophilic vinyl polymer (hydroxypropyl acrylate) onto a microporous hollow fiber membrane formed of polyvinylidene fluoride and having a pressure resistance of 600 kPa or more. The hollow fiber membrane was a multilayer microporous membrane having a coarse structure layer having a high porosity, being present on the inner surface of the membrane and having a thickness of 7.0 μm, and a fine structure layer having a low porosity and having a thickness of 80% of the thickness of the entire membrane, and the coarse structure layer and the fine structure layer being integrated. A human immunoglobulin G solution having a human immunoglobulin G concentration of 30 mg/ml (solvent: 0.1 M saline solution) was used as a model of an intermediate protein product. Following 3 kinds of virus solutions were respectively added to the human immunoglobulin G solution in an amount of 0.5 vol % to make 3 kinds of mixture solutions. The each mixture solution was pre-filtered through a hollow fiber membrane filter having a pore size of 35 nm ("PLANOVA (registered trademark) 35N" manufactured by Asahi Kasei Medical Co., Ltd.).

Virus solution 1: murine leukemia virus (A-MuLV) (Example 2, virus concentration: 5.0)

Virus solution 2: reovirus type 3 (Reo-3) (Example 3, virus concentration: 5.6)

Virus solution 3: minute virus of mice (MVM) (Example 4, virus concentration: 5.7)

These 3 kinds of virus solution-containing human immunoglobulin G solutions (each 30 mg/ml) were respectively subjected to dead-end filtration for 5 hours at an inlet pressure of 294 kPa using the above virus removal filter.

When adding A-MuLV (Example 2), the filtration rates measured after 1 hour, 2 hours, 3 hours, 4 hours, and 5 hours of filtration were 2.2 kg/m$^2$/Hr, 2.0 kg/m$^2$/Hr, 1.9 kg/m$^2$/Hr, 1.7 kg/m$^2$/Hr, and 1.6 kg/m$^2$/Hr, respectively. Specifically, the virus removal rate could be evaluated using a filtrate obtained at a high filtration rate of 1.0 kg/m$^2$/Hr or more in the all cases. The virus removal rates (LRV) measured using filtrates obtained respectively after 1, 3 and 5 hour of filtration were 4.5 or more in the all cases. A protein concentration of the intermediate protein product of 30 mg/ml, an inlet pressure of the virus removal filter of 294 kPa, and a filtration time of 5 hours or less could be determined as the operating conditions for the virus removal step.

When adding Reo-3 (Example 3), the filtration rates measured after 1 hour, 2 hours, 3 hours, 4 hours, and 5 hours of filtration were 2.5 kg/m$^2$/Hr, 2.3 kg/m$^2$/Hr, 2.1 kg/m$^2$/Hr, 2.0 kg/m$^2$/Hr, and 1.8 kg/m$^2$/Hr, respectively. Specifically, the virus removal rate could be evaluated using a filtrate obtained at a high filtration rate of 1.0 kg/m$^2$/Hr or more in the all cases. The virus removal rates (LRV) measured using a filtrate obtained after 1, 3 and 5 hour of filtration were 5.1 or more in the all cases. A protein concentration of the intermediate protein product of 30 mg/ml, an inlet pressure of the virus removal filter of 294 kPa, and a filtration time of 5 hours or less could be determined as the operating conditions for the virus removal step.

When adding MVM (Example 4), the filtration rates measured after 1 hour, 2 hours, 3 hours, 4 hours, and 5 hours of filtration were 2.4 kg/m$^2$/Hr, 2.3 kg/m$^2$/Hr. 2.1 kg/m$^2$/Hr. 2.0 kg/m$^2$/Hr, and 2.0 kg/m$^2$/Hr, respectively. Specifically, the virus removal rates could be evaluated using the filtrates obtained at a high filtration rate of 1.0 kg/m$^2$/Hr or more in the all cases. The virus removal rates (LRV) measured using a filtrate obtained after 1, 3 and 5 hour of filtration was 5.2 or more in the all cases. A protein concentration of the intermediate protein product of 30 mg/ml, an inlet pressure of the virus removal filter of 294 kPa, and a filtration time of 5 hours or less could be determined as the operating conditions for the virus removal step.

Comparative Example 1

A filter apparatus ("PLANOVA (registered trademark) 20N" manufactured by Asahi Kasei Medical Co., Ltd.) was used as a virus removal filter. The virus removal filter was formed of hollow fiber membrane (effective membrane area: 0.001 m$^2$) formed of cellulose (i.e., a thermoplastic resin was not contained) having a pressure resistance of 100 kPa, and had bamboo shoot-shaped nozzles which did not have pressure resistance of 600 kPa or more at the inlet and the outlet, wherein the space inside the container was divided by the hollow fiber membrane into an inlet-side space and an outlet-side space. A human immunoglobulin G solution having a human immunoglobulin G concentration of 30 mg/ml (solvent: 0.1 M saline solution) was used as a model of an intermediate protein product. After the addition of 0.5 vol % of a porcine parvovirus (PPV) solution to the human immunoglobulin G solution, the mixture was pre-filtered through a hollow fiber membrane filter having a pore size of 35 nm ("PLANOVA (registered trademark) 35N"). The immunoglobulin concentration and the PPV concentration after pre-filtration were 30 mg/ml and 5.9, respectively.

The PPV-containing human immunoglobulin G solution (30 mg/ml) was subjected to dead-end filtration for 5 hours at a maximum pressure of 98 kPa that can be applied to the cellulose membrane using the above virus removal filter.

The virus removal rates (LRV) measured using a filtrate obtained after 1 hour of filtration and a filtrate obtained after 5 hours of filtration were 5.4 or more in both cases. The filtration rates measured after 1 and 5 hours of filtration were 0.8 and 0.7 kg/m$^2$/Hr, (i.e., both were not reached to 1.0 kg/m$^2$/Hr). Therefore, the operating conditions for the virus removal step when producing a protein product could not be determined.

Comparative Example 2

A filter apparatus that was formed of a flat membrane (effective membrane area: 0.0003 m$^2$) formed of hydrophilized polyvinylidene fluoride having a pressure resistance of 600 kPa or more by the method disclosed in Example I of JP-B-7-71624 was used as a virus removal filter. The flat membrane had a fine structure layer that was formed on the surface thereof and had a thickness 20% or less with respect to the thickness of the entire membrane. The filter apparatus had a luer lock nozzle at the inlet, wherein the space inside the container was divided by the flat membrane into an inlet-side space and an outlet-side space. A human immunoglobulin G solution having a human immunoglobulin G concentration of 30 mg/ml (solvent: 0.1 M saline solution) was used as a model of an intermediate protein product. After the addition of 0.5 vol % of a porcine parvovirus (PPV) solution to the human immunoglobulin G solution, the mixture was pre-filtered through a hollow fiber membrane filter having a pore size of 35 nm ("PLANOVA (registered trademark) 35N"). The immunoglobulin concentration and the PPV concentration after pre-filtration were 30 mg/ml and 5.2, respectively.

The PPV-containing human immunoglobulin G solution (30 mg/ml) was subjected to dead-end filtration for 5 hours at a pressure of 294 kPa using the above virus removal filter. The virus concentration could not be measured using a filtrate obtained after 1 hour of filtration due to too low filtration rate (i.e., the filtration volume was too small). The virus removal rate (LRV) measured using a filtrate obtained after 3 hours of filtration was 4.0 or more. The filtration amount measured after 3 hours of filtration was 0.09 kg/m$^2$, the average filtration rate per hour of 0.03 kg/m$^2$/Hr, (i.e., was not reached 1.0 kg/m$^2$/Hr).

Therefore, the operating conditions for the virus removal step when producing a protein product could not be determined.

Comparative Example 3

A virus removal filter produced by the method disclosed in Example 1 of WO2004/035180 was used. Specifically, the virus removal filter was formed of a microporous hollow fiber membrane (effective membrane area: 0.001 m$^2$), and had a luer lock nozzle having a pressure resistance of 600 kPa or more at the inlet, wherein the space inside the container was divided by the hollow fiber membrane into an inlet-side space and an outlet-side space. The microporous hollow fiber membrane was formed only of a coarse structure layer which was obtained by graft-polymerizing (graft ratio: 10%) a hydrophilic vinyl polymer (hydroxypropyl acrylate) onto a microporous hollow fiber membrane formed of polyvinylidene fluoride having a pressure resistance of 600 kPa or more. A human immunoglobulin G solution having a human immunoglobulin G concentration of 30 mg/ml (solvent: 0.1 M saline solution) was used as a model of an intermediate protein product. 0.5 vol % of a porcine parvovirus (PPV) solution was added to the human immunoglobulin G solution. The PPV concentration was 6.0. The PPV-containing human immunoglobulin G solution (30 mg/ml) was subjected to dead-end filtration for 5 hours at a pressure of 294 kPa using the above virus removal filter. The average protein filtration rate measured after 1, 3 and 5 hours of filtration was 2.3, 2.2 and 2.0 kg/m²/Hr, respectively. The virus removal rate (LRV) measured using a filtrate obtained after 1, 3 and 5 hours of filtration were all 0.5 (i.e., not satisfied 3 or more). Therefore, the operating conditions for the virus removal step when producing a protein product could not be determined.

INDUSTRIAL APPLICABILITY

The filtration method according to the present invention can be collected the information useful for determining scale-uped practical operating conditions, facility design, and the like for the virus removal step in a production process of a protein product, such as antibody drug, recombinant protein drug, plasma product, or plasma fractionation product in a very small scale. Therefore, the filtration method according to the present invention is very useful for the protein product production industry.

The invention claimed is:

1. A filtration method for filtering an intermediate protein product having a predetermined protein concentration through a virus removal filter at a predetermined pressure, comprising:

(1) using a virus removal filter that comprises a container that has at least one inlet and at least one outlet, and a virus removal membrane that is made of a hydrophilized synthetic polymer for removing viruses from the intermediate protein product, the space inside the container is divided by the virus removal membrane into an inlet-side space and an outlet-side space, at least the inlet of the container has a nozzle having a fitting structure that has a pressure resistance of 600 kPa or more, and the virus removal membrane has an effective membrane area of 0.0001 to 0.03 m², (2) subjecting the intermediate protein product, which has a protein concentration of 30 to 100 mg/mL and has been pre-filtered, to dead-end filtration for 4 to 5 hours through the virus removal filter at an inlet pressure of 294 to 600 kPa and an average protein filtration rate of 1.6 kg/m²/Hr or more, and (3) obtaining a filtrate of the intermediate protein product having a virus removal rate (LRV: logarithmic reduction value) of 3 or more.

2. The filtration method according to claim 1, wherein the virus is selected from Parvoviridae, Retroviridae, Flaviviridae, Reoviridae, Paramyxoviridae, Herpesviridae, Picornaviridae, and Papovaviridae.

3. The filtration method according to claim 1, wherein the protein in the intermediate protein product is an immunoglobulin.

4. The filtration method according to claim 3, wherein the immunoglobulin is immunoglobulin G.

5. The filtration method according to claim 1, wherein the virus removal membrane is a hollow fiber virus removal membrane.

6. The filtration method according to claim 1, wherein the intermediate protein product was pre-filtered using a filter comprising a cellulose hollow fiber membrane.

* * * * *